United States Patent
Kleiner

(10) Patent No.: US 6,194,605 B1
(45) Date of Patent: Feb. 27, 2001

(54) PROCESS FOR PREPARING ALUMINUM SALTS OF DIALKYLPHOSPHINIC ACIDS AND DIPHOSPHINIC ACIDS

(75) Inventor: Hans-Jerg Kleiner, Kronberg (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/319,712

(22) PCT Filed: Dec. 2, 1997

(86) PCT No.: PCT/EP97/06743

§ 371 Date: Jul. 9, 1999

§ 102(e) Date: Jul. 9, 1999

(87) PCT Pub. No.: WO98/25937

PCT Pub. Date: Jun. 18, 1998

(30) Foreign Application Priority Data

Dec. 13, 1996 (DE) ............................................. 196 52 009

(51) Int. Cl.$^7$ ........................................................ C07F 9/30
(52) U.S. Cl. ................................................ 562/22; 562/8
(58) Field of Search ................................ 556/174; 562/8, 562/22

(56) References Cited

U.S. PATENT DOCUMENTS 3,401,185 * 9/1968 Meinhardt .

FOREIGN PATENT DOCUMENTS

699708 * 3/1996 (EP) .

OTHER PUBLICATIONS

CA:84:4051 abs of Zh Obshch Khim 45(9) pp 1946–8 by Razumov, 1975.*
CA:95:17327 abs of Transition Met Chem 6 (2) pp 79–82 by Mikulski, 1981.*
CA:78:147048 abs of Tethahedron Lett by Cook (7) pp 521–2, 1973.*

\* cited by examiner

*Primary Examiner*—Jean F. Vollano
(74) *Attorney, Agent, or Firm*—Connolly Bove Lodge & Hutz LLP

(57) ABSTRACT

A process for preparing aluminum salts (I) of dialkylphosphinic acids or (formula (II)) of alkylated diphosphinic acids

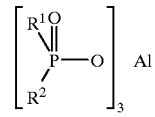

(I)

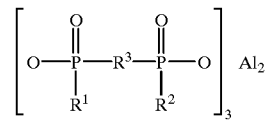

(II)

where $R^1$ and $R^2$ are a linear or branched $C_1$–$C_8$-alkyl radical and $R^3$ is a linear or branched $C_1$–$C_{10}$-alkylene radical or an arylene radical or an alkylarylene radical or an arylalkylene radical, which comprises reacting a dialkylphosphinic acid ester of the formula (III) or a diphosphinic acid ester of the formula (IV)

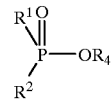

(III)

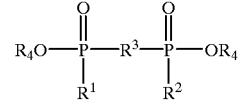

(IV)

where $R^1$, $R^2$ and $R^3$ are as defined above and $R^4$ is a linear or branched $C_1$–$C_8$-alkyl radical, in the presence of a saturated aliphatic monocarboxylic acid having a total of from 1 to 7 carbon atoms, with aluminum hydroxide at a temperature of from 150 to 350° C.

14 Claims, No Drawings

PROCESS FOR PREPARING ALUMINUM SALTS OF DIALKYLPHOSPHINIC ACIDS AND DIPHOSPHINIC ACIDS

This application is the national phase of PCT/EP97/06743, filed Dec. 2, 1997, now WO98/25937.

The invention relates to a process for preparing aluminum salts of dialkylphosphinic acids and diphosphinic acids.

Aluminum salts of phosphinic acids are useful flame retardants for polyester and polyamide molding compositions. They are prepared from the phosphinic acids in aqueous solution with metal carbonates, metal hydroxides or metal oxides (EP-A2-0 699 708).

In the prior art, conversion of phosphinic acid esters to the corresponding phosphinic acids to hydrolysis with an excess of water under pressure at 180° C. gives good yields only if the alcohol formed is removed as a mixture with water from the gas phase of the autoclave (Houben-Weyl, Methoden der organischen Chemie [Methods of Organic Chemistry], 1982, Vol. E2, page 142; DE-A1-27 45 982).

It was then found that the aluminum salts of phosphinic acids can be prepared in good yields from the corresponding esters with water and aluminum hydroxide, under pressure (DE 196 294 32.0).

This industrially useful process has the disadvantage of a relatively long reaction time, especially when longer-chained esters are used. For example, the hydrolysis of the butyl esters is markedly slower than that of the methyl esters, but they are simpler to prepare than the methyl esters.

The object was to find a process which does not have the disadvantages mentioned above and which can be implemented industrially without great cost and using auxiliary materials which are easily obtainable. The process should furthermore allow the desired products to be obtained both in high yield and in high purity.

Surprisingly, this object has been achieved by means of a process for preparing aluminum salts (formula (I)) of dialkylphosphinic acids or (formula (II)) of diphosphinic acids

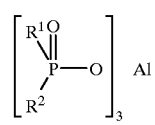
(I)

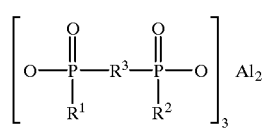
(II)

where

R$^1$ and R$^2$ are a linear or branched C$_1$–C$_8$-alkyl radical, preferably a linear or branched C$_1$–C$_4$-alkyl radical, such as methyl, ethyl, n-propyl, isobutyl, n-butyl, n-hexyl or phenyl and R$^3$ is a linear or branched C$_1$–C$_{10}$-alkylene radical, preferably a linear or branched C$_1$–C$_4$-alkylene radical, such as methylene, ethylene, n-propylene, isopropylene, n-butylene, n-decylene, or an arylene radical, such as phenylene or naphthylene; or an alkylarylene radical, such as methylphenylene, ethylphenylene or methylphenylenemethyl, or an arylalkylene radical, such as phenylmethylene or phenylethylene, which comprises reacting a dialkylphosphinic acid ester of the formula (III) or a diphosphinic acid ester of the formula (IV)

(III)

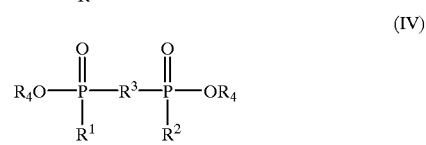
(IV)

where R$^1$, R$^2$ and R$^3$ are as defined above and R$^4$ is a linear or branched C$_1$–C$_8$-alkyl radical, preferably a linear or branched C$_4$–C$_6$-alkyl radical, in the presence of a saturated aliphatic monocarboxylic acid having a total of from 1 to 7 carbon atoms, with aluminum hydroxide at a temperature of from 150 to 350° C.

Surprisingly, the reaction times can be markedly reduced by the novel process. It gives the aluminum phosphinates in high purity and high yield. The process is technically simple, since to achieve the high yield it is not necessary to remove any byproducts, such as the esters produced from the monocarboxylic acids, from the reaction mixture.

Dialkylphosphinic acid esters which can be used for preparing the aluminum salts are in particular: methyl dimethylphosphinate, ethyl ethylmethylphosphinate, isobutyl ethylmethylphosphinate, n-butyl methylpropylphosphinate, amyl isobutylmethylphosphinate, isopropyl hexylmethylphosphinate, n-butyl methyloctylphosphinate, n-butyl methylphenylphosphinate and n-pentyl diphenylphosphinate. Diphosphinic acid esters which can be used for preparing the aluminum salts are in particular: di-n-butyl hexane-1,6-di(methylphosphinate) and diisobutyl benzene-1,4-di(methylphosphinate).

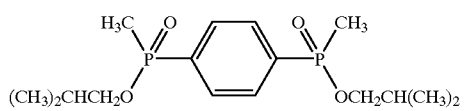

Dialkylphosphinic acid esters and diphosphinic acid esters are both referred to below as phosphinic acid esters.

Examples of saturated, aliphatic monocarboxylic acids are formic acid, acetic acid, propionic acid, n-butyric acid, isobutyric acid, n-valeric acid, isovaleric acid and mixtures of these acids. Acetic acid or propionic acid or mixtures of the same are particularly suitable.

Phosphinic acid esters, aliphatic monocarboxylic acids and aluminum hydroxide are known and familiar compounds, obtainable as widely marketed commercial products or easily accessible via preparation processes known in the prior art.

The aliphatic monocarboxylic acids are advantageously used in an amount of from about 50 to 300% by weight, preferably from 80 to 150% by weight, based in each case on the phosphinic acid ester used. If desired, the reaction mixture may also contain water, the ratio of monocarboxylic acid to water being in the range from 50:50 to 100:50.

The process of the present invention is generally carried out by heating the corresponding phosphinic acid esters with the aliphatic monocarboxylic acid and, if desired, water and stoichiometric amounts of aluminum hydroxide to a temperature of from 150 to 350° C., preferably from 180 to 250° C. in an autoclave, advantageously with continuous stirring. The reaction mixture is advantageously stirred for from 5 to 25 h, preferably from 5 to 10 h, to convert the phosphinic acid esters to the corresponding aluminum salts, the reaction times depending on the chain length of the ester groups of the phosphinic acid ester. Methyl esters, for example, react more readily than the butyl esters. During the reaction, the pressure in the autoclave rises to values in the range from 5 to 250 bar, preferably from 10 to 100 bar, in particular from 10 to 50 bar. As the end of the reaction approaches, the pressure remains approximately constant. After the reaction has ended, the reaction mixture is cooled and the aluminum phosphinates are then filtered off with suction. Finally, the resultant aluminum phosphinates are dried.

Surprisingly, it has been found that in order to achieve a good yield of the aluminum phosphinates, it is not necessary to remove from the reaction mixture the monocarboxylic esters which are produced in the reaction. The same is true if additional water is added to the reaction mixture. In this case also, it is not necessary to remove the monocarboxylic acid/alcohol mixture produced.

EXAMPLE 1

49.2 g (0.3 mol) of n-butyl ethylmethylphosphinate, 55 ml of acetic acid, 25 ml of water and 7.8 g (0.1 mol) of aluminum hydroxide are held at 220° C. for 20 hours in a 200 ml Hastelloy autoclave. The pressure rises to 25 bar. The reactants are then cooled, filtered off with suction, washed with acetic acid and dried at 140° C. in a vacuum drying cabinet. This gives 31.5 g of aluminum salt of ethylmethylphosphinic acid. The filtrate is freed from solvents in vacuo, and the residue is digested with water, giving a further 2 g and 33.5 g in total, corresponding to a yield of 96% of theory.

EXAMPLE 2

49.2 g (0.3 mol) of n-butyl ethylmethylphosphinate, 80 ml of acetic acid and 7.8 g (0.1 mol) of aluminum hydroxide are held at 220° C. for 10 hours in a 200 ml Hastelloy autoclave. The pressure rises to 24 bar. The reactants are then cooled, filtered off with suction, washed and dried at 140° C. in a vacuum drying cabinet. This gives 32 g of aluminum salt of ethylmethylphosphinic acid, corresponding to a yield of 92% of theory.

EXAMPLE 3

53.4 g (0.3 mol) of n-butyl methylpropylphosphinate, 55 ml of acetic acid, 25 ml of water and 7.8 g (0.1 mol) of aluminum hydroxide are held at 200° C. for 20 hours in a 200 ml Hastelloy autoclave. The pressure rises to 16 bar. The reaction is worked up as in Example 2. This gives 33 g of aluminum salt of methylpropylphosphinic acid, corresponding to a yield of 85% of theory.

EXAMPLE 4

65.6 g (0.4 mol) of n-butyl ethylmethylphosphinate, 55.2 g of formic acid and 10.4 g (0.133 mol) of aluminum hydroxide are brought to 190° C. over a period of 1.5 hours in a 200 ml Hastelloy autoclave. The pressure at 190° C. is 24 bar. The reaction mixture is then held for 3 hours at 200° C. and during this the pressure rises to 132 bar. The reactants are then cooled, and the pressure at room temperature is now 56 bar. After the customary work-up, this gives 35 g of aluminum salt of ethylmethylphosphinic acid. The filtrate is freed from low boilers in vacuo. After drying, a further 6 g remain behind. The total yield is therefore 89% of theory.

What is claimed is:

1. A process for preparing aluminum salts of dialkylphosphinic acids of formula (I) or alkylated diphosphinic acids of formula (II)

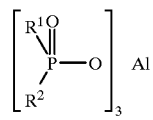

(I)

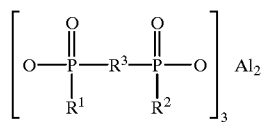

(II)

where
$R^1$ and $R^2$ are a linear or branched $C_1$–$C_8$-alkyl radical and
$R^3$ is a linear or branched $C_1$–$C_{10}$-alkylene radical or an arylene radical or an alkylarylene radical or an arylalkylene radical,
which comprises reacting a dialkylphosphinic acid ester of the formula (III) or a diphosphinic acid ester of the formula (IV)

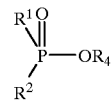

(III)

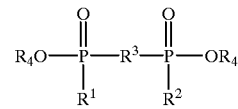

(IV)

where
$R^1$, $R^2$ and $R^3$ are as defined above and
$R^4$ is a linear or branched $C_1$–$C_8$-alkyl radical
in the presence of a solvent and reaction saturated aliphatic monocarboxylic acid having a total of from 1 to 7 carbon atoms, with aluminum hydroxide at a temperature of from 150 to 350° C. and the reaction is carried out in a closed pressure-resistant reaction vessel.

2. The process as claimed in claim 1, wherein
$R^1$ and $R^2$ are a linear or branched $C_1$–$C_4$-alkyl radical and
$R^3$ is a linear or branched $(C_1$–$C_4)$-alkylene radical or phenylene.

3. The process as claimed in claim 1, wherein the monocarboxylic acid is acetic acid or propionic acid or mixtures of these acids.

4. The process as claimed in claim 1, wherein, additionally, water is added to the reaction mixture.

5. The process as claimed in claim 1, wherein the pressure increases in the reaction vessel during the reaction.

6. The process as claimed in claim 1, wherein the pressure increases during the reaction to values in a range from 5 to 250 bar.

7. The process as claimed in claim 1, wherein, during the course of the reaction, no monocarboxylic esters produced by the reaction and, optionally, no alcohol produced, are removed from the reaction vessel.

8. The process as claimed in claim 1, wherein said reaction vessel is in an autoclave.

9. The process as claimed in claim 1, wherein the pressure is from 10 to 100 bar.

10. The process as claimed in claim 1, wherein the temperature is from 180 to 250° C.

11. The process as claimed in claim 1, wherein said aliphatic monocarboxylic acids are used in an amount from about 50 to 300% by weight based on the phosphinic acid ester used.

12. The process as claimed in claim 11, wherein the aliphatic monocarboxylic acid used is in an amount of from 80 to 150% by weight based on the phosphinic acid ester used.

13. The process as claimed in claim 10, wherein the reaction vessel is an autoclave and the pressure is in the range from 10 to 50 bar.

14. The process as claimed in claim 4, wherein the ratio of monocarboxylic acid to water is in the range from 50:50 to 100:50.

* * * * *